United States Patent
Anhalt et al.

(10) Patent No.: US 10,920,022 B2
(45) Date of Patent: Feb. 16, 2021

(54) METHOD FOR PRODUCING A PERMANENTLY COLORED OBJECT HAVING A SILICONE SURFACE AND COLORED OBJECT PRODUCED ACCORDING TO THE METHOD

(71) Applicant: OTTO BOCK HEALTHCARE GMBH, Duderstadt (DE)

(72) Inventors: Klaus-Peter Anhalt, Rhumspringe (DE); Martina Zuther, Bovenden (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 139 days.

(21) Appl. No.: 15/546,263

(22) PCT Filed: Jan. 22, 2016

(86) PCT No.: PCT/DE2016/100026
§ 371 (c)(1),
(2) Date: Jul. 25, 2017

(87) PCT Pub. No.: WO2016/119777
PCT Pub. Date: Aug. 4, 2016

(65) Prior Publication Data
US 2018/0066114 A1 Mar. 8, 2018

(30) Foreign Application Priority Data
Jan. 27, 2015 (DE) .................... 10 2015 001 075.1

(51) Int. Cl.
| | |
|---|---|
| *C08G 77/38* | (2006.01) |
| *A61F 2/50* | (2006.01) |
| *C08J 7/04* | (2020.01) |
| *C09D 7/41* | (2018.01) |
| *C08J 7/02* | (2006.01) |
| *B29C 71/02* | (2006.01) |
| *C08J 7/12* | (2006.01) |
| *C08K 5/00* | (2006.01) |
| *C09D 183/04* | (2006.01) |

(52) U.S. Cl.
CPC ................ *C08G 77/38* (2013.01); *A61F 2/50* (2013.01); *C08J 7/02* (2013.01); *C08J 7/0427* (2020.01); *C08J 7/08* (2013.01); *C08J 7/12* (2013.01); *C08K 5/0041* (2013.01); *C09D 7/41* (2018.01); *C09D 183/04* (2013.01); *A61F 2002/5001* (2013.01); *C08J 2383/04* (2013.01)

(58) Field of Classification Search
CPC .......... C08G 77/38; C09D 7/41; C09D 7/007; C09D 183/04; C08K 5/0041; C08J 7/047; C08J 2383/04; C08J 7/02; C08J 7/08; C08J 7/12; A61F 2002/5001; A61F 2/50
See application file for complete search history.

(56) References Cited

U.S. PATENT DOCUMENTS

| | | | |
|---|---|---|---|
| 5,370,688 A | 12/1994 | Schulz et al. | |
| 2003/0211338 A1* | 11/2003 | Frances | ..................... C08J 7/047 428/447 |
| 2006/0148985 A1* | 7/2006 | Karthauser | ........... C08F 283/12 525/100 |

FOREIGN PATENT DOCUMENTS

| | | |
|---|---|---|
| DE | 3636742 A1 | 5/1988 |
| EP | 0985388 A2 | 3/2000 |
| WO | 2014085913 A1 | 6/2014 |

OTHER PUBLICATIONS

F. Burgoyne, https://blogs.rsc.org/chipsandtips/2011/11/17/adding-colour-to-pmds-chips-for-enhanced-contrast/?doing_wp_cron=1588950125.0592560768127441406250, Nov. 17, 2011.*
SYLGARDTM 184 Silicone Elastomer Kit, found at https://www.dow.com/en-us/pdp.sylgard-184-silicone-elastomer-kit.01064291z.html, last visited May 8, 2020.*
SYLGARDTM 184 Silicone Elastomer Base, found at https://www.wpiinc.com/media/wysiwyg/pdf/SDS/sylgard184-base.pdf, last visited May 8, 2020.*
SYLGARDTM 184 Silicone Elastomer Curing Agent, found at https://www.wpiinc.com/media/wysiwyg/pdf/SDS/sylgard184-curing-agent.pdf, last visited May 8, 2020.*
MacCallum et al., Liquid-Infused Silicone As a Biofouling-Free Medical Material, ACS Biomater. Sci. Eng. 2015, 1, 43-51.*
PCT International Search Report for corresponding PCT International Patent Application No. PCT/DE2016/100026, dated May 27, 2016.

* cited by examiner

*Primary Examiner* — James M Mellott
(74) *Attorney, Agent, or Firm* — Holland & Hart, LLP

(57) ABSTRACT

A permanently colored object having a silicone surface which is produced by means of the following steps: a) mixing coloring substances with a still cross-linkable silicone in order to form an application mixture, b) swelling the silicone surface by means of a solvent, c) applying the application mixture to the silicone surface, and d) performing the cross-linking of the silicone of the application mixture, which silicone penetrates the silicone surface.

14 Claims, No Drawings

METHOD FOR PRODUCING A PERMANENTLY COLORED OBJECT HAVING A SILICONE SURFACE AND COLORED OBJECT PRODUCED ACCORDING TO THE METHOD

TECHNICAL FIELD

The invention relates to a method for manufacturing a permanently colored article having a silicone surface.

The invention further relates to a permanently color pigment-colored article having a silicone surface.

BACKGROUND

It is known that an article having a silicone surface, especially an article consisting entirely of silicone, is difficult to color because of the property of silicone not to take up other materials at its surface. Any coatings of color on the silicone surface are by dint of their weak bond to the silicone surface impermanent on being subjected to a mechanical stress.

The coloration problem presents particularly acutely with so-called cosmetic colors for prostheses, which are intended to emulate the skin texture and skin color including where applicable that of finger- or toenails as realistically as possible. Emulating the skin texture presupposes very fine creases and textures in the silicone surface, which must not be obscured by an applied layer of color.

It is known to pretreat a silicone surface, for example via a plasma treatment, a corona discharge by fluorination or by means of a primer. A color layer may then only be applied extremely thinly because otherwise it would obscure the laboriously and perhaps artfully produced texture on the silicone surface. However, a color layer of this type is insufficiently robust.

It is therefore known for such a silicone article, for example a silicone glove to emulate a natural hand surface, to be manufactured from a crystal-clear transparent silicone and, following an appropriate pretreatment, be colored on the inside surface of the glove. To this end, the glove is turned inside out, so its inside surface is on the outside and can be colored. After coloring, the colored outside surface is turned back to the inside, so the coloration is present on the inside and is protected from an external stress by the transparent layer of silicone. This method is very burdensome and does not allow for any correction to an off-shade hue, a faulty coloration due to some unsuccessful painting etc. Nor is it possible to subsequently apply a color layer to the crosslinked (fully vulcanized) silicone, since this would again require a pretreatment of the silicone surface.

SUMMARY

It is an object of the present invention to endow an article having a silicone surface with a coloration which is permanently durable and simple to apply.

We have found that this object is achieved according to the invention, by a method of the type in question, said method being characterized by the steps of:
a) mixing color-conferring substances with a still crosslinkable silicone to form an application mixture,
b) solvent swelling the silicone surface,
c) applying the application mixture to the silicone surface,
d) crosslinking the application mixture silicone as it penetrates into the silicone surface.

Optionally a drying step may be carried out before the crosslinking step.

The basis for the method of the invention is that the silicone surface swells up due to the solvent and thereby allows color-conferring substances to penetrate somewhat into the silicone surface together with the crosslinkable silicone of the application mixture. The swelling of the surface recedes during the subsequent drying and crosslinking, so the color-conferring substances are then in a thin layer of the silicone surface in a state of attachment, embedded in silicone particles formed by the crosslinking of the silicone present in the application mixture. The originally applied crosslinkable silicone bonds firmly to the swollen silicone surface, so the color-conferring substances can no longer be rubbed or washed off out of the surface. According to the invention, therefore, silicone material is applied to the swollen silicone surface in a reactive manner so that the reaction (crosslinking) of the silicone results in the formation of a firmly attached layer of color.

A permanent and rubfast coloration is thus attained for the silicone surface. It is readily apparent that any texturization of the surface is left intact by the method of the invention when the application mixture is both applied and crosslinked so as to penetrate into the swollen silicone surface and not form a coherent layer covering the surface or merely form a very thin layer of this type.

The crosslinkable application mixture silicone causing the attachment of the color-conferring substances in the silicone surface may be the same silicone of which the crosslinked silicone surface consists. This is not mandatory, however. What is required is merely the selection of such a silicone type as is compatible with the silicone surface, i.e., forms a firm bond with the crosslinked silicone surface as it itself undergoes crosslinking. This is actually also quite overwhelmingly the case with different types of silicone. A person skilled in the art knows which species of silicone are compatible with each other.

Preferably, the solvent for swelling the silicone surface is applied to the silicone surface as a constituent part of the application mixture. One possibility here is for the solvent for swelling the silicone surface to first be applied to the surface as a constituent part of the application mixture, so method steps b) and c) mentioned above are carried out conjointly, whereby there is no solvent on the silicone surface until the step of applying the application mixture. The step of applying the application mixture is effected without any activating pretreatment of the silicone surface. This silicone surface is merely cleaned, and freed of fats, oils and other disruptive constituents, before the method of the invention is carried out. There is no need for any further pretreatment.

The step of crosslinking the silicone of the application mixture is effected after the application of the application mixture, and the optionally performed drying step, under elevated temperature, i.e., preferably in an oven.

The application mixture may be applied by any desired method of application. Especially painting or spraying the silicone surface with the application mixture is especially suitable for cosmetic covers, such as silicone gloves or cosmetic foot parts.

The color-conferring substances, or colorants, may be soluble or insoluble substances, i.e., (insoluble) color pigments or (soluble) dyes. The colorants used may be organic or inorganic.

A coloration's color impression depends on the particular colorant used, but also on the amount of colorant in a surface region, i.e., on the thickness of the colorant layer. As this layer is reduced by abrasion, the coloration may change in its intensity, i.e., fade with abrasion. A further development of the present invention prevents this by the step of applying the reactive layer of colored silicone being followed by a step wherein the surface formed is, in a swollen state, again provided a reactive layer of silicone, but this layer is now transparent, especially colorlessly transparent. The reactive step of applying the transparent layer of silicone thus creates on the coloration a covering which by virtue of its transparency and irrespective of its thickness does not impair the coloration. When, therefore, the transparent layer is somewhat rubbed off in use, its thickness will decrease without this creating any visible effect on the color impression due to the coloration.

The step of applying the transparent, protective layer of silicone is carried out in the same way as the step of applying the colored layer of silicone for the purpose of producing the coloration. To firmly attach the protective layer of silicone, the surface formed by applying the colored layer of silicone is swollen up with a solvent and the silicone of the protective silicone layer is brought to a still crosslinkable state. The protective layer of silicone is thus likewise formed by an in situ crosslinking of the silicone to form the protective layer of silicone. In the same way as for the step of applying the colored layer of silicone, the solvent may be applied to the surface in advance or in a single-step process together with the corresponding reactive application mixture.

The abovementioned object is further achieved by a permanently color pigment-colored article having a silicone surface and wherein the color pigments have penetrated into a swollen surface of silicone down to a shallow depth of 1 µm in order of magnitude, and form a firmly attached layer of color as a result of the silicone undergoing crosslinking. The silicone surface in this embodiment is preferably free from any coherent layer covering it.

The permanently colored article may consist of any desired material and have a silicone surface. What is preferred, however, is an article which consists entirely of silicone, as may be the case for example with a preferred article in the form of a cosmetic cover for a prosthesis. Yet the description that the article consists entirely of silicone is not meant to foreclose the possibility that the article further comprises, on a surface remote from the silicone surface, a functional coating, for example a lubricity-enhancing coating which may consist of a textile or of a suitable polymeric layer, for example of Parylene (poly(para-xylylene)).

As explained above, the colored article may more particularly have a transparent covering layer of silicone above the coloration and acting as a protective layer for the coloration. It is further conceivable to form the transparent protective layer of some other material capable of being firmly bonded to the colored silicone. This embodiment is realizable, for example, with a transparent layer of Parylene, applied to the silicone surface by chemical vapor deposition (CVD).

The coloration which the invention provides to the silicone surface also works with fully crosslinked silicones, even with silicones stored for a year or longer, and this without prior activating pretreatment, such as primering, plasma treatment, corona discharge, fluorination, etc. Previously used silicone merely has to be thoroughly cleaned of any contamination and then is suitable for coloration by the method of the invention.

DETAILED DESCRIPTION

Example 1 Silicone Glove (Palm Surfaces Out/in)

634A58 isopropanol is used to clean a silicone glove of electrostatically adhering particles of dust and fuzzballs. A clean lint-free cloth or textile is used for this purpose. A drying time of 10 min at room temperature is allowed for because the isopropanol's evaporative cooling may cause the atmospheric humidity to condense out on the surface as water, which likewise has to be reevaporated.

The materials used are

| Solid | Silicone | LSR 3003-50 | 100.00% |
|---|---|---|---|
| Solvent | Silicone fluid | Q7-9180 | +278.08% |
| Color | Silicone color | Elastosil | |
| | white | RAL 9010 | +2.27% |
| | dark blue | RAL 5010 | +3.63% |
| | dark red | RAL3000 | +6.09% |
| | red | RAL3020 | +0.69% |

Note:
Solvent and color are reckoned as a percentage of the solids content.

Elastosil silicone color is thus used to produce a white, a dark blue, a dark-red and a red application mixture together with the silicone fluid as solvent.

The material used for the silicone glove is here referred to as solid silicone.

Of the color prepared, and kept in a fridge, about 5 ml are removed and applied to a nonabsorbent substrate (glass plate or a ceramic plate). A further approximately 7 ml of purely solvent (silicone fluid) is applied alongside. A long-hair synthetic brush is wetted with the same solvent and then a small amount of the color quantity prepared is taken with the brush from the plate and if necessary thinned with extra solvent in order to vary the color intensity and prolong the drying time. A blurred boundary between colors is additionally achieved thereby as desired.

Any desired mattness of the add-on may be influenced by dabbing off with a finely porous sponge or the like during the drying period, in which the silicone color is no longer fluent but not yet hard.

Example 2 Painting of Nails

634A5 cold cleaner (1685C fraction aliphatic hydrocarbonaceous mixture) is used to clean the silicone glove of electrostatically adhering dust particles and lint. A clean lint-free cloth or textile is used for this. The application mixture can be applied following a drying time of 5 minutes.

The materials used are

| Solid | Silicone | LSR 3003-50 | 100.00% |
|---|---|---|---|
| Solvent | Cold cleaner | | +278.08% |
| Color | Silicone color | Elastosil | |
| | white | RAL 9010 | +34.67% |
| | black | PAL 9011 | +0.79% |
| | dark blue | RAL 5010 | +1.76% |
| | yellow | RAL 1016 | +5.29% |
| | yellow | RAL 1021 | +1.26% |
| | dark red | RAL 3000 | +0.20% |

Note:
Solvent and color are reckoned as a percentage of the solids content.

Of the color mixture produced and kept in a fridge about 2 ml are removed and applied to a nonabsorbent substrate (a glass plate or a ceramic plate). Elastosil silicone color (Wacker Chemie, Munich) is a silicone-based pigmentary composition.

Then, a size 5/0 synthetic rigger brush is used to take up a small amount of the prepared color mixture off the plate and paint it directly onto the silicone in the nail region.

Painting the lunula and the tip of the nail requires a hiding stroke providing a clear boundary between colors. It is achieved when the formulation has a high pigment content and a low solvent content. So the formulation has to be made slow-evaporating via the nature of the solvent used in order to leave sufficient time for smooth application. This can also be achieved using a higher solvent of a fast-evaporating system, but the high solvent content would make it impossible to achieve the color intensity.

Example 3 Spraying Technique

634A81 silicone fluid is used to clean the silicone glove of electrostatically adhering particles of dust and fuzzballs. A clean lint-free cloth or textile is used for this purpose. Following a drying time of 10 min (as in Example 1), the application mixture can be applied by spraying. To this end, nail regions are covered up with nail varnish or the like in order that they may not be sprayed with the color. The materials used are

| Solid | Silicone | LSR 3003-50 | 100.00% |
|---|---|---|---|
| Solvent | Silicone fluid | Q7-9180 | +600.00% |
| Color | Silicone color | Elastosil | |
| | yellow | PAL 1021 | +10.00% |
| | dark red | RAL 3000 | +5.83% |
| | black | RAL 9011 | +12.71% |
| Delusterant | Silica | Acematt3300R | +1.89% |

\* manufacturer: Evonik Industries AG, Essen
Note:
solvent, color and delusterant are reckoned as a percentage of the solids content.

The color mixture is introduced into a spraygun or an airbrush system and applied at 2 bar pressure to the silicone surface in a plurality of passes. The protective varnish in the nail region is subsequently removed again using nail varnish remover and then the painting in the nail region is carried out as described in Example 2.

After painting or spraying, the article may dry at room temperature for 10 to 30 min and then crosslink/fully vulcanize in an oven at 120° C. for four hours or at 150° C. for two hours. This applies to all Examples 1 to 3.

We claim:

1. A method for manufacturing a permanently colored cosmetic cover having a crosslinked silicone surface with a texturization in the form of creases, the cosmetic cover having the shape of a prosthesis, the method comprising:
mixing color-conferring substances with a still crosslinkable silicone to form an application mixture;
solvent swelling the crosslinked silicone surface of the cosmetic cover;
applying the application mixture to the crosslinked silicone surface after the solvent swelling;
crosslinking the silicone of the application mixture as the application mixture penetrates into the crosslinked silicone surface to secure the application mixture to and permanently color the crosslinked silicone surface while leaving intact the creases of the crosslinked silicone surface.

2. The method as claimed in claim 1, further comprising drying the application mixture before the crosslinking.

3. The method as claimed in claim 1, wherein the application mixture is formed with the solvent used to swell the crosslinked silicone surface.

4. The method as claimed in claim 1, wherein the solvent for swelling the crosslinked silicone surface is applied to the crosslinked silicone surface as a constituent part of the application mixture.

5. The method as claimed in claim 1, wherein crosslinking the silicone of the application mixture is effected under elevated temperature.

6. The method as claimed in claim 1, wherein the application mixture is both applied and crosslinked so as to penetrate into the swollen crosslinked silicone surface and not form a coherent layer covering the crosslinked silicon surface.

7. The method as claimed in claim 1, wherein the application mixture is applied by painting or spraying.

8. The method as claimed in claim 1, wherein during crosslinking the silicon of the application mixture, applying a transparent layer to the silicon surface, the transparent layer comprising a crosslinkable silicone.

9. The method as claimed in claim 1, wherein after crosslinking the silicon of the application mixture, solvent swelling a resulting surface, and applying a transparent layer to the resulting surface, the transparent layer comprising a crosslinkable silicone.

10. A method for manufacturing a permanently colored cosmetic cover that is formed as a glove or cosmetic foot part, the method comprising:
forming a crosslinked silicone surface having a plurality of creases;
forming an application mixture having color-conferring substances and an uncrosslinked silicone;
solvent swelling the crosslinked silicone surface;
applying the application mixture to the solvent swelled crosslinked silicone surface;
penetrating the application mixture into the solvent swelled crosslinked silicone surface;
crosslinking the silicone of the application mixture that is penetrated into the solvent swelled silicone surface to permanently color the crosslinked silicone surface and connect the application mixture to the crosslinked silicone surface while leaving intact the plurality of creases of the crosslinked silicone surface.

11. The method as claimed in claim 10, further comprising drying the application mixture before the crosslinking.

12. The method as claimed in claim 10, wherein the application mixture is formed with the solvent used to swell the silicone surface.

13. The method as claimed in claim 10, wherein the solvent for swelling the crosslinked silicone surface is applied to the crosslinked silicone surface as a constituent part of the application mixture.

14. A method for manufacturing a permanently colored cosmetic cover having a crosslinked silicone surface with a texturization in the form of creases, the cosmetic cover having the shape of a prosthesis, the method comprising:
mixing color-conferring substances with a still crosslinkable silicone to form an application mixture;
solvent swelling the crosslinked silicone surface of the cosmetic cover;
applying the application mixture to the crosslinked silicone surface after the solvent swelling;
crosslinking the silicone of the application mixture as the application mixture penetrates into the crosslinked silicone surface to secure the application mixture to and permanently color the crosslinked silicone surface while leaving intact the creases of the crosslinked silicone surface to give the cosmetic cover the appearance of at least one of skin texture and skin color.

* * * * *